United States Patent

Hart et al.

[11] 4,307,729
[45] Dec. 29, 1981

[54] OPTICAL DIGITIZER FOR MEASURING SPIROMETER OUTPUT

[75] Inventors: Russell F. Hart, Blue Grass; Joan M. Gluth; Gerald A. Brumm, both of Davenport, all of Iowa

[73] Assignee: The Bendix Corporation, Southfield, Mich.

[21] Appl. No.: 109,386

[22] Filed: Jan. 3, 1980

[51] Int. Cl.³ .............................................. A61B 5/08
[52] U.S. Cl. ...................................... 128/727; 73/239
[58] Field of Search ............................... 128/725–729; 73/232, 239, 231 R; 272/99

[56] References Cited

U.S. PATENT DOCUMENTS

| | | | |
|---|---|---|---|
| 3,217,539 | 11/1965 | Owen et al. | 73/231 R |
| 3,680,378 | 8/1972 | Aurilio et al. | 128/726 X |
| 3,922,525 | 11/1975 | Kozak et al. | 128/725 X |
| 3,985,124 | 10/1976 | Coleman | 128/727 |

FOREIGN PATENT DOCUMENTS 197712 12/1977 U.S.S.R. ............................. 128/726

OTHER PUBLICATIONS

Teodorescu, "Optoelectronic . . . Sensor for Medical Use", Electronic Engineering, Jun. 1977, p. 29.

Primary Examiner—Lee S. Cohen
Attorney, Agent, or Firm—W. G. Christoforo; Bruce L. Lamb

[57] ABSTRACT

A spirometer includes an expansible chamber of the piston type fitted with an indicia strip. The indicia comprise two columns of alternating light and dark bars. The columns are offset from one another by one-half the thickness of a bar and are respectively viewed by two photodetectors which generate signals which are shifted 90° from one another as the columns pass through their respective fields of view. The signals are continuously sampled as digital words and consecutive words are compared to determine whether a counter should be incremented or decremented by one or two counts.

6 Claims, 6 Drawing Figures

OPTICAL DIGITIZER FOR MEASURING SPIROMETER OUTPUT

FIELD OF THE INVENTION

This invention relates to spirometry and more particularly to means for producing an electrical signal which is proportional to forced vital lung capacity as measured by a spirometer.

BACKGROUND OF THE INVENTION

Spirometers are used to measure forced vital lung capacity usually of a human subject. A spirometer now in general use includes an expansible chamber having a movable piston fitted with a molded rolling rubber seal which comprises a movable boundary of the expansible chamber. The subject expires air through a tube connected to an opening into the chamber thereby causing the piston to move, expanding the chamber. A recording surface in the form of a removable card is attached to the piston and a pen is drawn across the face of the card at a constant velocity as the subject exhales into the expansible chamber. There is thus obtained on the card a plot of the volume of expiration flow as a function of time. The disadvantage of this type of spirometer is that its readout is purely in mechanical format and hence not readily adaptable to interfacing with computing devices which can perform certain pertinent lung function calculations, given the spirometer measurements.

It is important in using spirometers that any device used to measure the movement of the expansible chamber piston exert an absolute minimum influence thereon so as to prevent distortion of the measurement. For the same reason any means used to convert spirometer mechanical measurements to an electrical format should exert an absolute minimum influence on the quantitative measurements.

According to the present invention a spirometer has a fixed case, a portion of which forms the fixed boundaries of an expansible chamber, and a movable piston fitted with a molded rubber seal which forms the movable boundaries of the expansible chamber so that the piston and fixed case move relative to one another as a function of the quantity of air exhaled by the subject. The piston and case are coupled to one another by means such as a radiant energy transducer affixed to one and indicia on the other which pass through the field of view of the transducer as the piston moves relative to the case and to which the transducer responds to generate a first distinctive cyclically repeating series of digital numbers when movement is in a first direction and a second distinctive cyclically repeating series of digital numbers when movement is in the opposite direction. A logic circuit is provided which combines one of the numbers with the next generated number to form a new number which is analyzed in a look-up table to determine whether a counter should be incremented or decremented. The counter thereby contains a number which is a function of the quantity of air exhaled by the subject.

In the embodiment to be described the radiant energy transducer comprises a pair of reflective object or photo detectors affixed adjacent to one another to the case or to brackets affixed to the case and which view individual fields of view through which indicia in the form of alternate light and dark bars pass as the piston moves. The signal from either one of the reflective object detectors is a lower level sine wave which is conditioned and converted to a rectangular wave. The fields of view are off-set relative to the indicia so that the wave from one detector is out of phase with the wave from the other detector. There is thus instantaneously available from the detectors a two digit word, one digit from each detector, and a distinctive cyclically repeating sequence of four such words for continuous movement of the piston in one direction and the same four words in a cyclically repeating sequence of words for movement in the opposite direction except that the sequence is reversed. As will be explained, two such successively generated words unambiguously denotes that the piston has not moved or has moved less than the indicia pitch, or that the piston has moved one indicia pitch and the direction in which it moved. As explained above, two such successive words are combined to form a new word which is searched for in a look-up table to thereby control the aforementioned counter.

More specifically, the indicia comprise two columns of alternating light and dark bars. The longitudinal axes of the columns are arranged to be parallel to the line of piston movement so that each column passes under a respective reflective object sensor as the chamber expands or contracts. The bars of one column are slightly displaced with respect to the bars of the other column or alternately, a single column is used and the reflective object sensors are slightly displaced with respect to one another along the line of piston movement to allow the logic tests to monitor the direction of piston travel. The alternating light and dark bars of the columns passing under the reflective object sensors cause the outputs of these sensors to switch between the high logic state, (1), and their low logic state, (0). These transitions are counted in appropriate electronic circuits comprised of the aforementioned look-up table and counter to provide a measure of total piston displacement and hence a present volume or differential volume of the expansible chamber in the form of an electrical signal.

It is the main object of this invention to provide an accurate spirometer having an electrical output.

One advantage of the invention is that it can easily be retrofitted to existing spirometers.

Another advantage of the invention is that it allows a spirometer to generate an electrical output signal which can be directly coupled into computing circuits.

A further advantage of the invention is that it provides a means for use in a spirometer for generating an electrical spirometer output signal without mechanically loading the moving elements of the spirometer.

PREFERRED EMBODIMENT OF THE INVENTION

Figure 1:
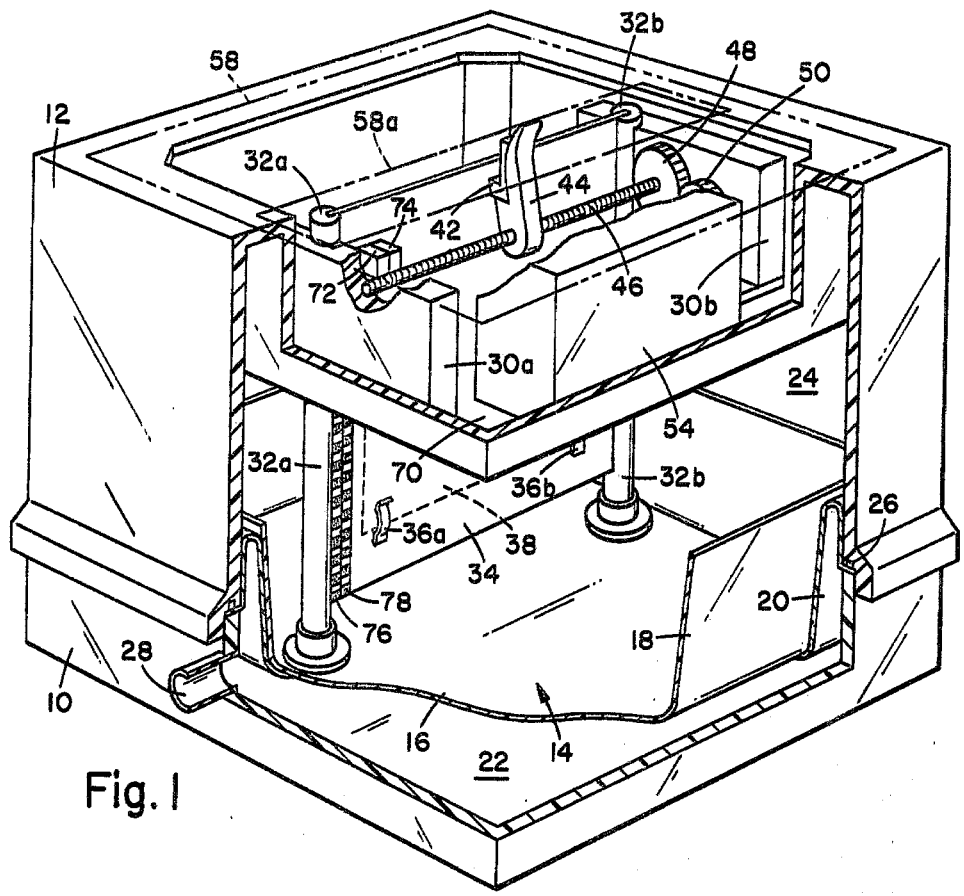
FIG. 1 is an isometric view of a spirometer cut away to show the preferred embodiment of the invention.

Referring to FIG. 1, a conventional spirometer is divided into two major sections, a lower casing 10 and an upper casing 12. A piston 14, preferably a single piece molding, forming a flat rectangular plate 16 having upturned sides 18, is located within the casings. A flexible rolling seal 20 surrounds piston 14 and separates the inside of the device into a lower expansible chamber 22 and an upper chamber 24 which is open to the atmosphere. Rolling seal 20 is preferably made of a single piece of molded silicone rubber. The rolling seal 20 is clamped at its edges between the upper and lower casings 10 and 12 to provide for ease of assembling and ease of disassembling for cleaning and maintenance, and to seal the lower chamber from the atmosphere. A lip 26 around the edge of the seal aids this sealing function.

Exhaled from a subject, air enters the device through an opening 28. Attached to the opening is a conduit preferably made of a flexible tubing (not shown) to allow the subject to take a comfortable position during a test. Opening 28 introduces expired air into the expansible lower chamber 22 to thereby displace piston 14 in a vertical direction.

Fastened to opposing sides of piston 14 are posts 32a and 32b which ride in guides 30a and 30b respectively, as chamber 22 changes volume, thereby constraining piston 14 to move in a straight vertical line. Guides 30a and 30b are fastened to upper casing 12. A thin metallic plate 34 is fastened between posts 32a and 32b so that it moves with piston 14. Two clips 36a and 36b are mounted to the surface of plate 34 for holding a paper card 38. As known to those skilled in the art, during a forced vital lung capacity test, that is, as the subject expires air into chamber 22, a pen 42 on a carrier 44 is moved at a constant speed and in a horizontal line across card 34 by a threaded rod 46 rotated by a constant speed motor 54 through gears 48 and 50 and upon which is threaded pen carrier 44. Carrier 44 is constrained against rotation about the threaded rod but is free to move horizontally thereon, thus it moves horizontally from one vertical edge of card 38 to the other as the threaded rod is rotated. Of course, as piston 14 moves carrying card 38 the pen traces a curve thereon which is a measure of the volume of chamber 22 with respect to time, which is also a measure of forced vital lung capacity.

Upper casing 12 includes an integral recessed platform 70 on which is mounted the pen drive mechanism 54. A rectangular opening in platform 70 is provided for plate 34 posts 32a and 32b together with card 38 which rise through the aforesaid as chamber 22 expands. A similar opening is provided in a cover (whose outline 58a is shown in phantom) for the same reason and to permit card 38 to be retrieved and renewed. Various controls, connectors and the counter to be discussed below are mounted in the cover and hence are not seen. The physical arrangement of these items does not comprise any part of this invention, however, and need not be described further.

Optical reflective object sensors 72 and 74 are mounted side by side on platform 70 and view indicia such as columns 76 and 78 of vertically stacked alternating horizontal light and dark bars. As can be seen the bars of column 76 are slightly offset vertically with respect to the bars of column 78. Sensor 72 is positioned to illuminate and view the bars of column 76 and sensor 74 is positioned to illuminate and view the bars of column 78 throughout the effective range of travel of plate 34. Control circuitry for sensors 72 and 74 is packaged on a printed circuit board mounted to the bottom side of the cover whose outline is shown at 58.

Columns 76 and 78 are disposed on a common adhesive-backed tape which is affixed to plate 34. The tape material should be long-lifed, stable and tough and should resist distortion. Scotchcal brand tape has been successfully used for this purpose. Scotchcal is a trademark of the 3 M Company of St. Paul, Minnesota, U.S.A.

Figure 2:
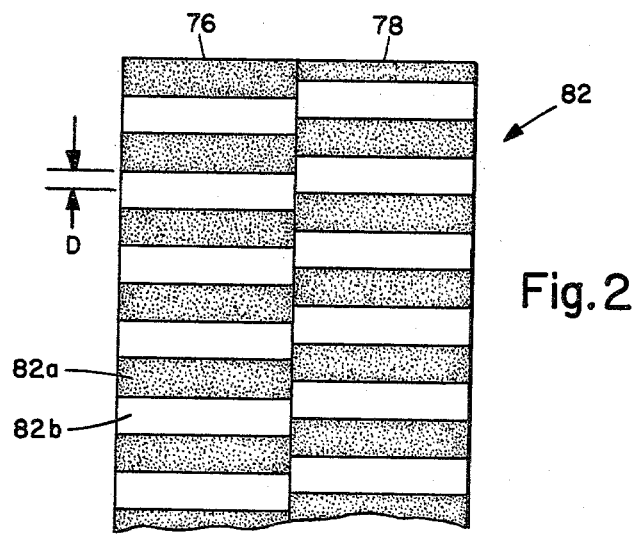
FIG. 2 shows in greater detail the optical indicia used in the preferred embodiment of the invention.

Refer now to FIG. 2 which shows columns 76 and 78 of FIG. 1 disposed on a Scotchcal brand tape 82. Scotchcal brand tape is an adhesive-backed aluminum foil tape having a black coating. Chemically etching the black coating by conventional means in selected areas leaves the desired pattern of alternating dark and light bars where the dark bars are the original black coated material and the light bars are bare aluminum. The dark bars are generally designated 82a and the light bars 82b. The bars are preferably of equal height and width. In a unit actually built there were about five bars per centimeter. The bars of column 76 are vertically displaced an amount D from the bars of column 78 to permit the logic circuits of the invention to determine whether plate 34 of FIG. 1 is moving up or down as will be more fully explained below.

Figure 3:
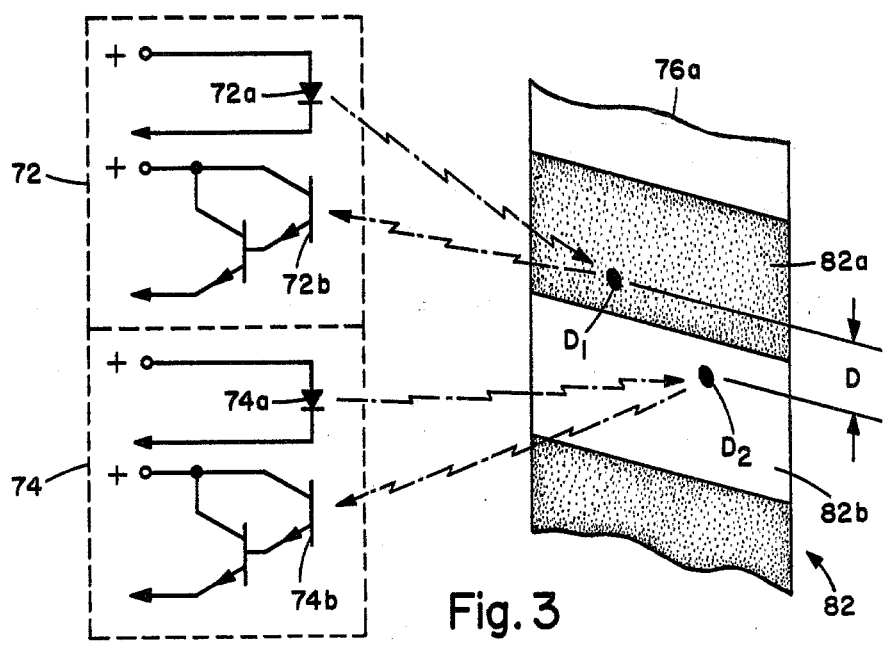
FIG. 3 illustrates an alternate form of optical coupling.

FIG. 3 schematically illustrates an alternative form of the invention which uses a single column 76a of alternating dark and light bars 82a and 82b respectively imprinted on tape 82. In this case sensors 72 and 74 are generally arranged horizontally as shown in the embodiment of FIG. 1 but displaced slightly vertically. Sensor 72 is seen to be comprised of a light emitting diode 72a which is directed, for example, so as to illuminate an area D1 on column 76a. A light sensor such as phototransistor 72b is arranged to view that same area and to thus generate a logical zero output when area D1 is on a dark bar 82a and to generate a logical 1 output when area D1 is on a light bar 82b. In like manner, sensor 74 is comprised of a light emitting diode 74a and a light sensor 74b. Light emitting diode 74a is directed at an area D2 which is spaced a vertical distance D from area D1. Light sensor 74b, which is arranged to view area D2, generates a logical zero when D2 is on a dark bar 82a and a logical 1 when D2 is on a light bar 82b. The distances D in FIGS. 2 and 3 are suitably identical to produce identical results from the two embodiments illustrated and preferably equal to about one half the height of a bar.

Figure 4:
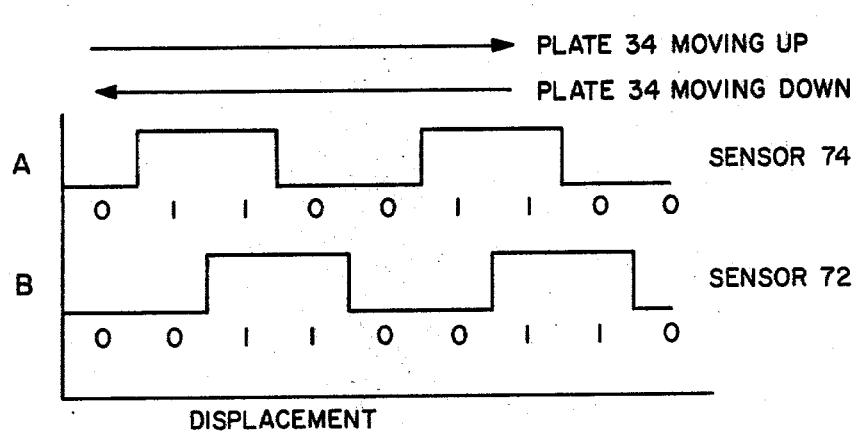
FIG. 4 is a chart which helps to explain how the direction of piston movement is monitored.

The direction of motion of plate 34 of FIG. 1 is determined in logic circuits by an examination of the sequence of the signals generated by sensors 72 and 74. This can be easily explained with reference to FIG. 4 which assumes the specific embodiments of FIGS. 2 or 3 where the fields of view of the sensors are vertically offset, for example, by vertically offsetting the sensors or the indicia. Thus, as plate 34 moves upward the output from sensor 74 will lead the output from sensor 72 by some phase angle equivalent to the offset between the two columns. This is seen clearly in FIG. 4, reference to which should now be made, where the signals from sensors 74 and 72 are seen respectively as curves A and B drawn to a common plate 34 displacement reference. The curves are read from left to right in the case of a rising plate 34 and from right to left for a falling plate. It can be seen that the sensors together can generate a total of 4 two-bit digital words equivalent to 0, 1, 2, 3 and that these words are generated in a distinct sequence depending upon whether plae 34 is moving up or down. In particular, for this embodiment, the repeating sequence of equivalent words for the plate moving up is 2, 3, 1, 0 and the repeating sequence of equivalent words for the plate moving down is 0, 1, 3, 2. Thus it can be seen by considering two consecutive different words from sensors 72 and 74 it is possible to determine the direction of plate movement, that is, whether volume 22 of FIG. 1 is expanding or contracting.

Figure 5:
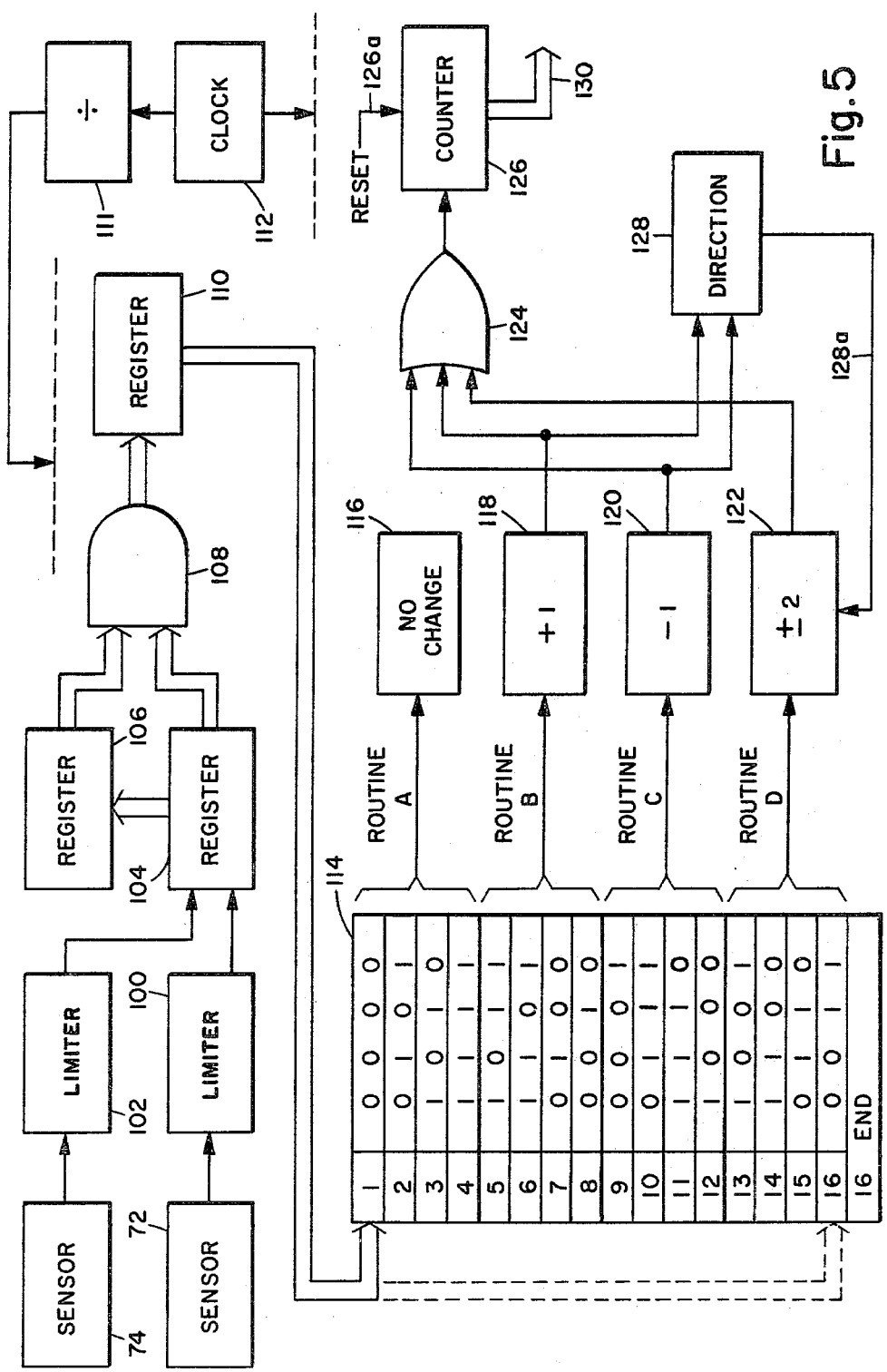
FIG. 5 is a block diagram of the electrical logic circuits used in this embodiment of the invention.

The logic circuits which examine the sequence of signals generated by sensors 72 and 74 to determine the direction of motion of plate 34 are comprised of a microprocessor, a block diagram of which is seen in FIG. 5, reference to which figure should now be made. The logic circuits comprise a two-bit storage means such as register 104 which receives the parallel output, signals from sensors 72 and 74 respectively via conditioning or limiting circuits 100 and 102 which convert the sine wave output signals from sensors 72 and 74 to rectangular waves. The resulting rectangular waves are sampled into register 104 in response to clock pulses received from an internal clock 112 via divider 111. Simultaneously the previous contents of register 104 are stored into two-bit storage means such as register 106. Also, simultaneously, the word entering register 104 and the word entering register 106 are combined by gate means 108 into a single four-bit word which is stored in four-bit register 110. The second two-bits of this four-bit word comprise the two-bit word now stored in register 106 and the first two-bits comprise the two-bit word now stored in register 104. The word stored in register 110 is searched through a look-up table in memory 114 in response to clock pulses from clock 112. When the word in register 110 is found, an appropriate routine is initiated by memory 114. For example, assume first that plate 34 of FIG. 1 does not move or does not move enough between successive clocks from divider 111 to change the word in register 104. In that event the words in registers 104 and 106 will be identical to one another so that the resultant word in register 110 will be one of those shown in positions 1 through 4 of memory 114, namely, 0000, 0101, 1010, or 1111. In that case, routine A, illustrated as box 116, will be initiated. Assume now that plate 34 moves up so that the word in register 104 changes. In that event the word in register 110 will be one of those shown at positions 5 through 8 of memory 114, namely, 1011, 1101, 0100 or 0010. The search for the word in register 110 in memory 114 will thus initiate routine B, here illustrated by box 118. Assume now that plate 34 moves down. In that event the word in register 110 will be one of those found at positions 9 through 12 of memory 114, namely, 0001, 0111, 1110, 1000. Routine C, here illustrated as box 120, will thus be initiated.

As will be known to those skilled in the art, the word stored in register 110 is searched for in memory 114 at a rate of one step for each clock pulse from clock 112. Thus, divider 111 has been provided to ensure that the search through memory 114 is complete before the word in register 110 changes. In a unit actually built the rate of clock 112 was such that sampling pulses issued from divider 111 at a rate of 10 kHz.

Occasionally, the sensors or circuits will miss one of the digital number transitions as plate 35 moves up or down rapidly thus introducing a possible error. This error can be obviated by examining the word in register 110 for miscounts. Specifically, and referring briefly again to the table of FIG. 4, it can be seen that a missed count will manifest itself as a missed two-bit word in the table. Thus, the resulting word, in the case of a missed count, in register 110 of FIG. 5 will be one of those shown at positions 13 through 16 of memory 114, namely, 1001, 1100, 0110 or 0011. Closer examination of the table of FIG. 4 will show that the words at positions 13 to 16 of memory 114 do not uniquely identify whether plate 34 is moving up or down. All that is known when such a word is identified in memory 114 is that routine D, here illustrated as box 122, will be initiated. A directional flag, illustrated as box 128, is provided as an indication whether plate 34 is moving up or down as will be explained below.

A counter 126 contains a count which is a measure of the distance travelled by plate 34 and hence a measure of the volume of chamber 22 of FIG. 1. Counter 126 is reset to an initial value, suitably zero, by a signal on line 126a which can be derived from a reset pushbutton mounted on the case of the spirometer. The counter accumulates counts obtained from gate means 124. When routine A is initiated, as occurs when there is no minimum movement of plate 334, there is no input to gate 124 and the count in counter 126 remains constant. When routine B is initiated, indicating that plate 34 has moved up by one increment, a single count is applied through gate 124 to counter 126. When routine C is initiated, indicating that plate 34 has moved down one increment, the signal from box 120 applied to gate means 124 causes counter 126 to decrement by one count. It will be remembered that if routine D is initiated, direction of plate 34 is not immediately determinable and it is merely known thereby that two counts are to be added to or decremented from counter 126. The sense of these counts is determined by direction flag 128, which is suitably an equivalent flip-flop which is set or reset by the signals from routine B, 118, or routine C, 120. More specifically, this portion of the logic circuit assumes that a miscount will occur only if plate 34 is moving rapidly and thus has not reversed direction of movement between clock pulses on line 112. Thus, the two counts from routine D, 122, are to be added or decremented in accordance with whether the previous count was added or decremented. A state signal from direction flag 128 on line 128a, which is dependent upon whether the previous count was added to or decremented from counter 126, is applied to routine D, 122 and directs the two counts therefrom applied to gate means 124 to be added to or decremented from counter 126 as appropriate. The state or count in counter 126 is available for loading into suitable computer circuits via a line 130.

Figure 6:
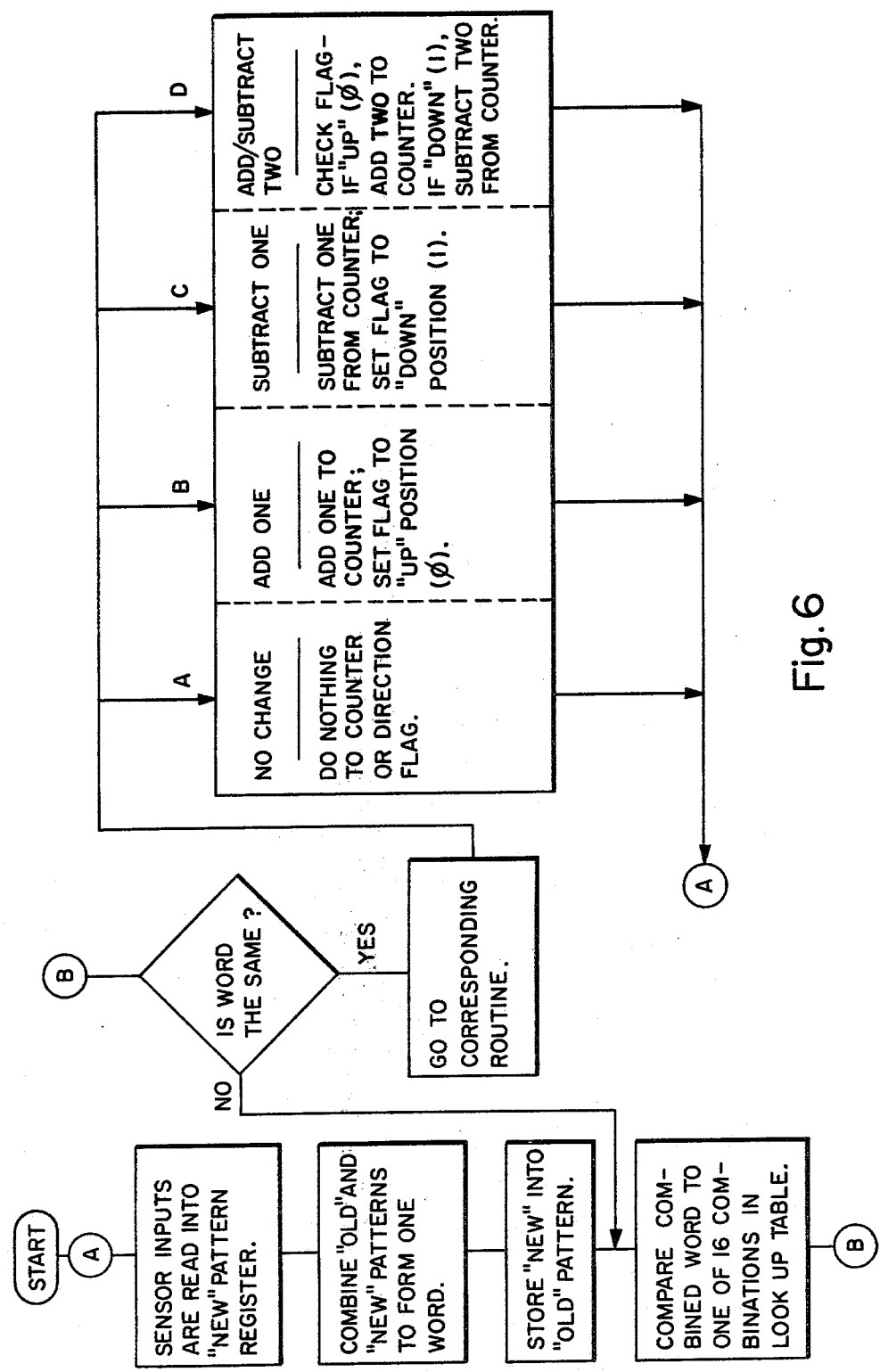
FIG. 6 is a flow diagram of the logic of the invention.

The logic circuits of FIG. 5 are preferably embodied in a microprocessor. The flow diagram of such a microprocessor is shown at FIG. 6 which together with the entire disclosure herein will permit one skilled in the art to construct the microprocessor used in the disclosed embodiments. FIG. 6 is self-explanatory and need not be further described.

Having described various embodiments of our invention, certain alternations and modifications thereof should now suggest themselves to one skilled in the art. For example, the indicia and transducer can be interchanged so that the indicia is affixed to the spirometer case and the transducer carried by the moving card. As another example, the coupling of the moving piston to the fixed case can be other than optical, it merely being necessary that the coupling means exert a minimum influence on movement of the piston and that appropriate signals be generated. Thus, a magnetic coupling can be used wherein magnetic transducers respond to the relative movement of magnetic indicia. It should also now be obvious to one skilled in the art that the digital electrical signal generated by the improved spirometer described herein can be applied to computing circuits to provide an analysis of volume of expiration flow as a function of time in addition to total volume of flow. Accordingly, we intend to limit our invention only by the true spirit and scope of the appended claims.

The invention claimed is:

1. In a spirometer having a casing, piston means within said casing constrained to rectilinear motion, and means forming an air tight seal between said piston means and said casing, said casing, piston means and seal means together forming a substantially air tight expansible chamber, said casing having an opening through which expiratory flow is introduced into said expansible chamber, the introduction of expiratory flow producing movement of said piston means, an improvement comprising:

optically detectable indicia fixed with respect to one of said piston means and said casing;

first and second photodetector means, fixed with respect to the other of said piston means and said casing for generating output signals in response to relative motion of said optically detectable indicia with respect to said first and second photodetector means, said first photodetector means being arranged to observe a first field of view and said second photodetector means being arranged to observe a second field of view, said indicia passing through said field of view as said piston means moves, said fields of view being arranged so that the output signals from said first photodetector means are out of phase with the output signals from said second photodetector means;

means for converting said output signals to a repeating sequence of n-bit digital words;

means for periodically combining one n-bit digital word with a previous n-bit digital word to form a 2 n-bit digital word;

a counter; and means responsive to said 2 n-bit digital word for incrementing or decrementing said counter, said counter thereby generating an electrical signal related to the volume of said expansible chamber.

2. The spirometer of claim 1 wherein said optically detectable indicia comprise a column of alternating light and dark bars, said column having a longitudinal axis generally coinciding with the line of motion of said piston means, said fields of view being offset from one another along said longitudinal axis.

3. The spirometer of claim 1 wherein said optically detectable indicia comprise first and second parallel columns, each of alternating light and dark bars, the bars of said first column being offset along the columns longitudinal axis with respect to the bars of said second column, said longitudinal axis generally coinciding with the line of motion of said piston means, said first column passing through said first field of view and said second column passing through said second field of view as said piston means moves.

4. The spirometer of claims 2 or 3 wherein said first and second photodetector means include light emitting diodes for illuminating said indicia.

5. The spirometer of claims 2 or 3 wherein said output signals are about 90° out of phase.

6. The spirometer of claim 5 wherein said output signals are rectangular waves and n is equal to 2 there thereby being four different 2-bit digital words in said repeating sequence, the words occurring in order as said piston means moves in one direction and in a reverse order as said piston means moves in the opposite direction indicative of expansion or contraction respectively of said expansible chamber.

* * * * *